US 6,575,745 B2

(12) United States Patent
Meller et al.

(10) Patent No.: US 6,575,745 B2
(45) Date of Patent: *Jun. 10, 2003

(54) TITANIUM ALLOY INTRAOSSEOUS ANESTHESIA DELIVERY DEVICE

(75) Inventors: Moshe Meller, Haifa (IL); Michael Feldman, Tom River, NJ (US)

(73) Assignee: Tulsa Dental Products Inc., Tulsa, OK (US)

( * ) Notice: Subject to any disclaimer, the term of this patent is extended or adjusted under 35 U.S.C. 154(b) by 33 days.

This patent is subject to a terminal disclaimer.

(21) Appl. No.: 09/730,345

(22) Filed: Dec. 5, 2000

(65) Prior Publication Data

US 2002/0068256 A1 Jun. 6, 2002

(51) Int. Cl.⁷ ................................................ A61M 5/32
(52) U.S. Cl. ......................... 433/80; 604/264; 604/272
(58) Field of Search ..................... 433/80, 165; 606/80; 604/272

(56) References Cited

U.S. PATENT DOCUMENTS

| | | |
|---|---|---|
| 1,123,730 A | 1/1915 | Greenfield |
| 1,539,637 A | 5/1925 | Bronner |
| 2,317,648 A | 4/1943 | Siqveland |
| 2,442,033 A | 5/1948 | Brantly et al. |
| 3,406,685 A | 10/1968 | May |
| 3,750,667 A | 8/1973 | Pshenichny et al. |
| 3,778,904 A | 12/1973 | Melde |
| RE27,923 E | 2/1974 | Bentov |
| 3,893,445 A | 7/1975 | Hofsess |
| 4,002,169 A | 1/1977 | Cupler, II |
| 4,021,920 A | 5/1977 | Kirschner et al. |
| 4,193,197 A | 3/1980 | Kuris et al. |
| 4,220,446 A | 9/1980 | Walker |
| 4,306,570 A | 12/1981 | Matthews |
| 4,513,754 A | 4/1985 | Lee |
| 4,678,471 A | 7/1987 | Noble et al. |

(List continued on next page.)

FOREIGN PATENT DOCUMENTS

GB        1430092        3/1976

OTHER PUBLICATIONS

Data Sheet: WIRE—NITINOL; p. 131; publication date unknown; www.smallparts.com; e-mail parts@smallparts.com.
Pearce, Jr. "Intraosseous Injection For Profound Anesthesia of the Lower Molar" (1 page).
Cannell et al "Intraosseous Injections of Lignocaine Local Anaesthetics" British Dental Journal, vol. 141, Jul. 20, 1976, pp. 48–50.
Liliental "A Clinical Appraisal of Intraosseous Dental Anesthesia", Oral Surg. vol. 39, No. 5, May, 1975, pp. 692–697.
Bourke "Intra–Osseous Anaesthesia", Dent. Anaesthesia And Sedation, vol. 3, No. 2, Jul. 1974, pp. 13–18.
Dorfman "Predictable and Effective Anesthesia Utilizing Intraosseous Injections" (3 pages).
Leonard "The Efficacy of an Intraosseous Injection System of Delivering Local Anesthetic", JADA, vol. 126, Jan., 1995, pp. 81–86.
Magnes "Intraosseous Anesthesia", Anesthesia Progress, Nov. 1968, pp. 264–267.
Garfunkel Et Al. "Intralignamentry–Intraosseous Anesthesia", Int. J. Oral Surg. 1983; pp. 334–339.
Biddulph "Intraosseous Anesthesia For Dental Procedures", The Arizona Dental Journal (2 pages).

*Primary Examiner*—Ralph A. Lewis
(74) *Attorney, Agent, or Firm*—Frishauf, Holtz, Goodman & Chick, P.C.

(57) ABSTRACT

An intraosseous delivery apparatus having a perforating member that is made of a titanium alloy whose flexibility, wearability and cutting ability is greater than that of conventional hardened stainless steel.

7 Claims, 1 Drawing Sheet

U.S. PATENT DOCUMENTS

| | | |
|---|---|---|
| 4,747,824 A | 5/1988 | Spinello |
| 4,787,893 A | 11/1988 | Villette |
| 4,869,717 A | 9/1989 | Adair |
| 4,944,677 A | 7/1990 | Alexandre |
| 4,973,247 A | 11/1990 | Varnes et al. |
| 5,049,150 A | 9/1991 | Cozad |
| 5,057,013 A | 10/1991 | Dillon |
| 5,085,631 A | 2/1992 | Leighton |
| 5,125,838 A | 6/1992 | Seigneurin |
| 5,173,050 A | 12/1992 | Dillon |
| 5,201,656 A | 4/1993 | Sicurelli |
| 5,203,866 A | 4/1993 | Islam |
| 5,261,877 A | 11/1993 | Fine et al. |
| 5,275,563 A | 1/1994 | Cohen et al. |
| 5,304,140 A * | 4/1994 | Kugo et al. |
| 5,312,345 A | 5/1994 | Cole |
| 5,312,375 A | 5/1994 | Gurmarnik |
| 5,341,816 A | 8/1994 | Allen |
| 5,374,270 A | 12/1994 | McGuire et al. |
| 5,389,070 A | 2/1995 | Morell |
| 5,406,940 A | 4/1995 | Melzer et al. |
| 5,423,823 A | 6/1995 | Schmieding |
| 5,423,824 A | 6/1995 | Akerfeldt et al. |
| 5,429,504 A | 7/1995 | Peltier et al. |
| 5,431,655 A | 7/1995 | Melker et al. |
| 5,432,824 A | 7/1995 | Akerfeldt et al. |
| 5,484,442 A | 1/1996 | Melker et al. |
| 5,489,208 A | 2/1996 | Mandell |
| 5,527,205 A | 6/1996 | Heath et al. |
| 5,554,154 A | 9/1996 | Rosenberg |
| 5,601,559 A | 2/1997 | Melker et al. |
| 5,653,590 A * | 8/1997 | Heath et al. ................. 433/102 |
| 5,762,639 A | 6/1998 | Gibbs |
| 5,779,708 A | 7/1998 | Wu |
| 5,814,049 A | 9/1998 | Pratt et al. |
| 6,042,585 A * | 3/2000 | Norman ...................... 606/104 |
| 6,135,769 A | 10/2000 | Kwan |
| 6,210,376 B1 * | 4/2001 | Grayson ..................... 604/264 |
| 6,217,561 B1 * | 4/2001 | Gibbs ........................ 604/264 |
| 6,241,710 B1 * | 6/2001 | Van Tassel et al. ......... 604/272 |
| 6,247,928 B1 * | 6/2001 | Meller et al. ................. 433/80 |
| 6,273,715 B1 * | 8/2001 | Meller et al. ................. 433/80 |
| 6,287,114 B1 * | 9/2001 | Meller et al. ................. 433/80 |

* cited by examiner

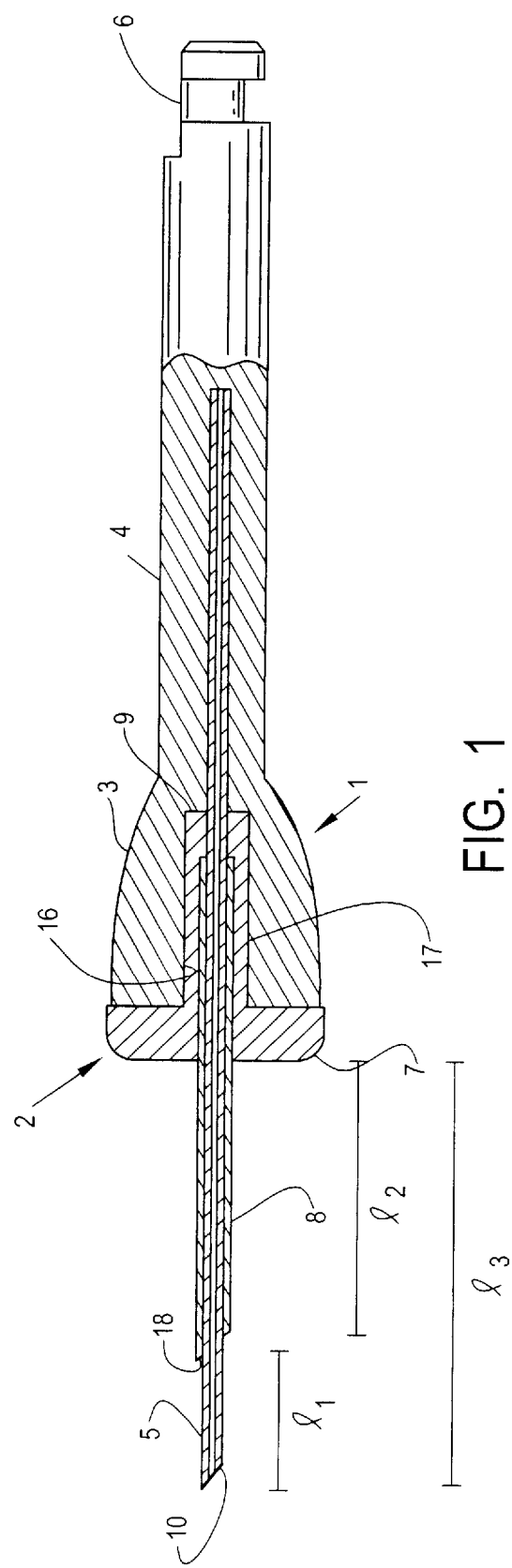

TITANIUM ALLOY INTRAOSSEOUS ANESTHESIA DELIVERY DEVICE

BACKGROUND OF THE INVENTION

The present invention relates to an improved intraosseous anesthesia delivery device.

There exist a variety of intraosseous anesthesia delivery devices and methods, including those disclosed in U.S. Pat. No. 2,317,648 to Siqveland, U.S. Pat. No. 4,944,677 to Alexandre, U.S. Pat. No. 4,423,824 to Akerfeldt et al, U.S. Pat. No. 5,762,639 to Gibbs, U.S. Pat. No. 5,779,708 to Wu, U.S. Pat. No. 5,057,013 to Dillon, U.S. Pat. No. 5,173,050 to Dillon and U.S. Pat. No. 6,135,769 to Kwan.

Additional intraosseous anesthesia delivery devices and methods are disclosed in the Applicant's earlier U.S. application Ser. No. 09/165,010, PCT Application US99/07728, U.S. application Ser. No. 09/328,682, and U.S. application Ser. No. 09/329,022, the entire contents of each of which are incorporated herein by reference.

All known present day anesthesia delivery devices and methods, however, generally utilize a perforating member such as a hypodermic injection needle or drill bit member that is made of hardened stainless steel. Under poor conditions, such hardened stainless steel perforating members may cause significant burning of bone tissue and/or may break. And if either of these events occurs, there is a high risk of infection and/or other complications.

OBJECTS OF THE INVENTION

It is an object of the present invention to provide an intraosseous anesthesia delivery device whose perforating member has improved flexibility and wearability and improved cutting ability, and which thereby improves operability and reduces the risk of infection and/or other complications.

DETAILED DESCRIPTION

Figure 1:
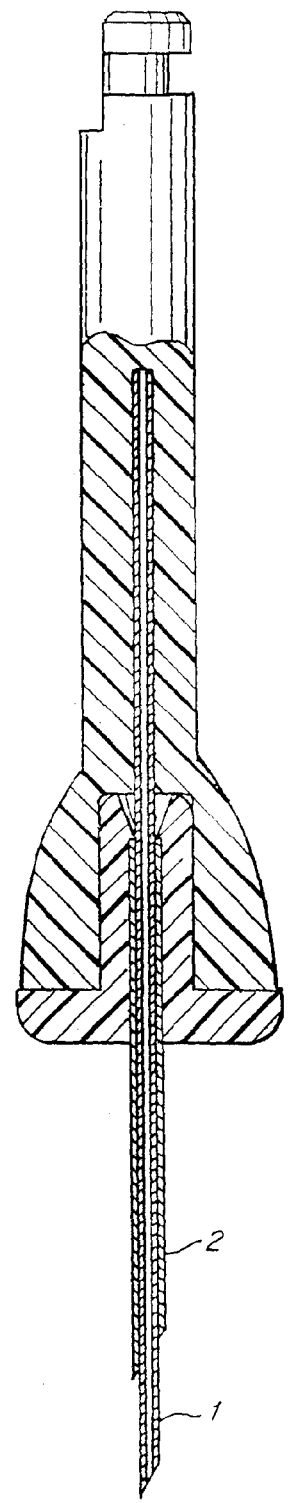
FIG. 1 is a partial sectional view of an intraosseous anesthesia delivery device to which the present invention may be adapted.

In order to achieve the above mentioned objects, the present invention provides an anesthesia delivery apparatus which utilizes a bone perforating member made of a titanium alloy that comprises at least 10% titanium. Preferably, the perforating member is made of a titanium alloy that comprises at least 40% titanium. For example, according to a preferred embodiment, the present invention utilizes a perforating member made of a NITINOL alloy whose composition is typically 55%–56% nickel and 44%–45% titanium.

In one specific preferred embodiment, the alloy consists of 44% titanium and 56% nickel and no other appreciable amount of any other ingredient which could adversely effect the purity required for dental instruments.

Still more specifically, the perforating member of the present invention may be made, for example, from NITINOL Type 1, Part No. U-NW-015 available at www.smallparts.com.

The present invention, however, may utilize any material containing titanium whose flexibility, wearability and cutting ability is greater than that of conventional hardened stainless steel.

The use of a titanium alloy achieves numerous significant advantageous effects. First, the flexibility and wearability of the perforating member is increased, thereby reducing its chances of breakage. In fact, the use of a titanium alloy enables the perforating member of the present invention to change direction during drilling and to still hit its target, even if from the side-and to do so without breaking. Second, the cutting ability of a titanium alloy perforating member is much higher than that of a conventional stainless steel perforating member, and the friction between a titanium alloy perforating member and the bone tissue into which the perforating member is being drilled is significantly reduced. This reduces the temperatures generated during drilling and lowers the amount of bone tissue burning, thereby reducing the chances of infection and/or other complications. And third, the use of a titanium alloy perforating member enables drilling to be performed in a much wider range of speeds than is available when a conventional hardened stainless steel perforating member is used. More specifically, the use of a titanium alloy perforating member enables drilling to be performed at speeds between approximately 2000 rpm and approximately 20,000 rpm, with a preferred speed of approximately 10,000 rpm, whereas the use of a conventional hardened stainless steel perforating member typically requires higher speeds on the order of 15,000 rpm.

FIG. 1 shows an example of a disposable intraosseous anesthesia delivery device to which the present invention may be adapted. This disposable anesthesia delivery device is described in detail in each of U.S. application Ser. No. 09/328,682 now issued as U.S. Pat. No. 6,273,715, and U.S. application Ser. No. 09/329,022 now issued as U.S. Pat. No. 6,287,114, whose entire contents (as indicated hereinabove) are incorporated herein by reference.

The essential feature of the present invention is that the perforating member 1 (referred to as drill 5 in each of U.S. application Ser. No. 09/328,682, and U.S. application Ser. No. 09/329,022) is made of a material containing titanium whose flexibility, wearability and cutting ability is greater than that of conventional hardened stainless steel.

As shown in FIG. 1, the perforating member 1 is hollow, but the present invention also equally applies to the case where the perforating member is solid.

In addition, it is noted that outer sleeve 2 (referred to as hollow sleeve 8 in each of U.S. application Ser. No. 09/328,682, and U.S. application Ser. No. 09/329,022) may also be made of a titanium alloy, or may alternatively be made of conventional hardened stainless steel.

Still further, it is noted that the present invention is applicable to an intraosseous delivery device which utilizes a perforation member that is adapted to independently penetrate bone—i.e., without an outer sleeve thereon and/or without a stylet inserted therein.

Indeed, the essential feature of the present invention—namely, the use of a perforating member made of a titanium alloy—may be adapted to any of the devices shown in the Applicant's earlier U.S. application Ser. No. 09/165,010, PCT Application US99/07728, U.S. application Ser. No. 09/328,682, and U.S. application Ser. No. 09/329,022, and/or to any of the devices shown in U.S. Pat. No. 2,317,648 to Siqveland, U.S. Pat. No. 4,944,677 to Alexandre, U.S. Pat. No. 5,432,824 to Akerfeldt et al, U.S. Pat. No. 5,762,639 to Gibbs, U.S. Pat. No. 5,779,708 to Wu, U.S. Pat. No. 5,057,013 to Dillon, U.S. Pat. No. 5,173,050 to Dillon and U.S. Pat. No. 6,135,769 to Kwan.

What is claimed is:

1. An intraosseous fluid delivery apparatus comprising:

a hollow sleeve; and a perforating member adapted to be coupled to a drill and to be fitted inside said hollow sleeve and to extend beyond a distal end of said hollow sleeve, wherein the perforating member is made of a titanium alloy comprising at least 10% titanium.

2. The intraosseous fluid delivery apparatus according to claim 1, wherein the titanium alloy comprises at least 40% titanium.

3. The intraosseous fluid delivery apparatus according to claim 1, wherein the titanium alloy is a NITINOL alloy comprising 55%–56% nickel and 44%–45% titanium.

4. The intraosseous fluid delivery apparatus according to claim 1, wherein the titanium alloy consists of 44% titanium and 56% nickel and no other appreciable amount of any other ingredient.

5. An intraosseous fluid delivery method comprising:

removably coupling a perforating member to a drill;

removably fitting the perforating member inside a hollow sleeve so as to extend beyond a distal end of said hollow sleeve;

applying a bone penetration force from the drill to the perforating member so as to drill a hole in a bone;

removing the perforating member from the hollow sleeve; and introducing a fluid directly into the hole drilled in the bone via the hollow sleeve;

wherein the perforating member is made of a titanium alloy comprising at least 10% titanium.

6. The intraosseous delivery method according to claim 5, wherein the bone penetration force is applied by rotating the perforating member at a speed between approximately 2000 rpm and approximately 20,000 rpm.

7. The intraosseous delivery method according to claim 5, wherein the bone penetration force is applied by rotating the perforating member at a speed of approximately 10,000 rpm.

* * * * *

UNITED STATES PATENT AND TRADEMARK OFFICE
CERTIFICATE OF CORRECTION

PATENT NO.  : 6,575,745 B2
DATED       : June 10, 2003
INVENTOR(S) : Moshe Meller It is certified that error appears in the above-identified patent and that said Letters Patent is hereby corrected as shown below:

<u>Drawings,</u>
Substitute the attached corrected Fig. 1.

Signed and Sealed this

Thirtieth Day of December, 2003

JAMES E. ROGAN
*Director of the United States Patent and Trademark Office*